(12) United States Patent
Johnston et al.

(10) Patent No.: US 7,855,303 B2
(45) Date of Patent: Dec. 21, 2010

(54) INTEGRATED PROCESS FOR THE PRODUCTION OF VINYL ACETATE FROM ACETIC ACID VIA ETHYLENE

(75) Inventors: Victor J. Johnston, Houston, TX (US); Laiyuan Chen, Houston, TX (US); James H. Zink, League City, TX (US); Josefina T. Chapman, Houston, TX (US); Barbara F. Kimmich, League City, TX (US); Deborah R. Repman, Lake Jackson, TX (US)

(73) Assignee: Celanese International Corporation, Dallas, TX (US)

( * ) Notice: Subject to any disclaimer, the term of this patent is extended or adjusted under 35 U.S.C. 154(b) by 0 days.

(21) Appl. No.: 12/291,949

(22) Filed: Nov. 14, 2008

(65) Prior Publication Data

US 2010/0125148 A1    May 20, 2010

(51) Int. Cl.
C07C 67/00 (2006.01)
C07C 67/05 (2006.01)
(52) U.S. Cl. ................................. 560/241; 560/243
(58) Field of Classification Search .................. None
See application file for complete search history.

(56) References Cited

U.S. PATENT DOCUMENTS

| | | | |
|---|---|---|---|
| 2,021,698 A | 11/1935 | Perkins | |
| 2,425,389 A | 8/1947 | Oxley et al. | |
| 2,607,807 A * | 8/1952 | Ford | 568/885 |
| 2,859,241 A | 11/1958 | Schnizer | |
| 2,882,244 A | 4/1959 | Milton | 252/455 |
| 3,130,007 A | 4/1964 | Breck | 23/113 |
| 3,702,886 A | 11/1972 | Argauer et al. | 423/328 |
| 4,270,015 A | 5/1981 | Knifton | 585/324 |
| 4,398,039 A | 8/1983 | Pesa et al. | |
| 4,399,305 A | 8/1983 | Schreck | 562/607 |
| 4,421,939 A | 12/1983 | Kiff et al. | |
| 4,480,115 A | 10/1984 | McGinnis | |
| 4,517,391 A * | 5/1985 | Schuster et al. | 568/885 |
| 4,620,050 A | 10/1986 | Cognion et al. | 585/640 |
| 4,696,596 A | 9/1987 | Russell | 403/321 |
| 4,843,170 A | 6/1989 | Isshiki et al. | |
| 4,873,392 A * | 10/1989 | Le Van Mao | 585/640 |
| 4,933,204 A | 6/1990 | Warren, Jr. et al. | 427/53.1 |
| 4,978,778 A | 12/1990 | Isshiki et al. | |
| 5,149,680 A | 9/1992 | Kitson et al. | |
| 5,185,308 A | 2/1993 | Bartley et al. | 502/170 |
| RE35,377 E | 11/1996 | Steinberg et al. | 518/704 |
| 5,674,800 A * | 10/1997 | Abel et al. | 502/326 |
| 5,691,267 A | 11/1997 | Nicolau et al. | 502/330 |
| 5,719,315 A | 2/1998 | Tustin et al. | |
| 5,731,456 A | 3/1998 | Tustin et al. | |
| 5,821,111 A | 10/1998 | Grady et al. | 435/252.5 |
| 6,040,474 A * | 3/2000 | Jobson et al. | 560/243 |
| 6,114,571 A | 9/2000 | Abel et al. | 560/245 |
| 6,121,498 A | 9/2000 | Tustin et al. | |
| 6,232,352 B1 | 5/2001 | Vidalin | 518/700 |
| 6,476,261 B2 * | 11/2002 | Ellis et al. | 562/606 |
| 6,603,038 B1 | 8/2003 | Hagemeyer et al. | 560/241.1 |
| 6,657,078 B2 | 12/2003 | Scates et al. | 562/519 |
| 6,685,754 B2 | 2/2004 | Kindig et al. | 48/210 |
| 6,696,596 B1 * | 2/2004 | Herzog et al. | 560/245 |
| 6,852,877 B1 | 2/2005 | Zeyss et al. | 560/241 |
| 2003/0018229 A1 | 1/2003 | Vaughn et al. | |
| 2006/0106246 A1 * | 5/2006 | Warner et al. | 560/241 |
| 2010/0030001 A1 | 2/2010 | Chen et al. | |
| 2010/0030002 A1 | 2/2010 | Johnston et al. | |

FOREIGN PATENT DOCUMENTS

| | | |
|---|---|---|
| EP | 175558 | 3/1986 |
| EP | 192587 | 8/1986 |
| EP | 0 330 853 | 9/1989 |
| GB | 1 559 540 | 1/1980 |
| JP | 2006-116439 A | 11/2006 |
| WO | 99/08791 | 2/1999 |
| WO | 99/08791 A1 | 2/1999 |
| WO | 02092541 A1 | 11/2002 |
| WO | 2010014152 * | 2/2010 |
| WO | 2010014152 A1 | 2/2010 |

OTHER PUBLICATIONS

Mol. Sieves Pap. Conf., 1967, 78, Soc. Chem. Ind. London, by D. Domine and J. Quobex.
U.S. Appl. No. 12/221,137, filed Jul. 31, 2008, Johnston et al.
U.S. Appl. No. 12/221,138, filed Jul. 31, 2008, Johnston et al.

(Continued)

Primary Examiner—Karl J Puttlitz

(57) ABSTRACT

This invention provides an integrated two stage economical process for the production of vinyl acetate monomer (VAM) from acetic acid in the vapor phase. First, acetic acid is selectively hydrogenated over a hydrogenating catalyst composition to form ethylene either in a single reactor zone or in a dual rector zone wherein the intermediate hydrogenated products are either dehydrated and/or cracked to form ethylene. In a subsequent second stage so formed ethylene is reacted with molecular oxygen and acetic acid over a suitable catalyst to form VAM. In an embodiment of this invention reaction of acetic acid and hydrogen over a hydrogenation catalyst and subsequent reaction over a dehydration catalyst selectively produces ethylene, which is further mixed with acetic acid and molecular oxygen and reacted over a supported palladium/gold/potassium catalyst.

12 Claims, No Drawings

OTHER PUBLICATIONS

International Search Report and Written Opinion for PCT/US2009/004191 mailed Mar. 24, 2010 (13 pages).

International Search Report and Written Opinion for PCT/US2009/006016 mailed Apr. 29, 2010 (10 pages).

Tustin et al., Synthesis of vinyl acetate monomer from synthesis gas, Catalyst Today, vol. 58(4) (2000) pp. 281-291.

Roscher, "Ullmann's Encyclopedia of Industrial Chemistry - Vinyl Esters, "Ullmann's Encyclopedia of Industrial Chemistry (2000) pp. 1-18.

* cited by examiner

INTEGRATED PROCESS FOR THE PRODUCTION OF VINYL ACETATE FROM ACETIC ACID VIA ETHYLENE

FIELD OF THE INVENTION

The present invention relates generally to an integrated process for the production of vinyl acetate monomer (VAM) from the reaction of acetic acid and ethylene. More specifically, the present invention relates to an integrated process in which acetic acid is converted to ethylene in a first reaction zone with the ethylene further reacted with additional acetic acid in another reaction zone to form VAM. The present invention also relates to an integrated process including hydrogenating acetic acid utilizing a first catalyst composition in a first reaction zone and dehydrating or cracking hydrogenated intermediates with a second catalyst in a second reaction zone to form ethylene. The ethylene from the second reaction zone is reacted with additional acetic acid in a third reaction zone to produce VAM.

BACKGROUND

There is a long felt need for an economically viable process to manufacture VAM from acetic acid without utilizing independently sourced ethylene. VAM is an important monomer in the production of polyvinyl acetate and polyvinyl alcohol products among other important uses. Due to fluctuating natural gas and crude oil prices contributing to variations in the cost of conventionally produced petroleum or natural gas-sourced ethylene, an important feedstock used in the manufacture of VAM, the need for alternative cost-effective sources of ethylene in order to produce VAM becomes all the greater.

It has now been found that VAM can be produced without utilizing independently sourced ethylene. For example, it is well known that synthesis gas can be reduced to methanol, which is in fact one preferred way to manufacture methanol. Methanol thus formed can then be converted selectively to acetic acid under catalytic carbonylation conditions which is a preferred process for the manufacture of acetic acid. The acetic acid thus formed then can be selectively converted to ethylene under suitable catalytic conditions. Although there are no known preferred processes for such a conversion, the prior art does provide certain processes for such a conversion of acetic acid to ethylene albeit at low conversions and yields thus making it industrially unsuitable.

For instance, it has been reported that ethylene can be produced from various ethyl esters in the gas phase in the temperature range of 150-300° C. over zeolite catalysts. The types of ethyl esters that can be employed include ethyl esters of formic acid, acetic acid and propionic acid. See, for example, U.S. Pat. No. 4,620,050 to Cognion et al., where selectivity is reported to be acceptable.

U.S. Pat. No. 4,270,015 to Knifton describes obtaining ethylene involving a two-step process in which a mixture of carbon monoxide and hydrogen (commonly known as synthesis gas (syngas)) is reacted with a carboxylic acid containing 2 to 4 carbon atoms to form the corresponding ethyl ester of said carboxylic acid which is subsequently pyrolyzed in a quartz reactor at elevated temperatures in the range of about 200° to 600° C. to obtain ethylene.

U.S. Pat. No. 4,399,305 to Schreck describes obtaining high purity ethylene from ethyl acetate employing a cracking catalyst composed of a perfluorosulfonic acid resin commercially sold under the trademark NAFION® by E. I. DuPont de Nemours & Co.

Once ethylene has been produced, further processing with acetic acid is required for conversion to VAM as demonstrated in U.S. Pat. No. 6,696,596 to Herzog et al., incorporated herein by reference in its entirety, which indicates that it is well known to manufacture VAM in a reaction in the gas phase with acetic acid and oxygen or oxygen containing gasses over fixed-bed catalysts.

Additional examples of the manufacture of VAM from ethylene and acetic acid are set forth in U.S. Pat. No. 6,040,474 to Jobson et al. which describes the manufacture of acetic acid and/or vinyl acetate using two reaction zones wherein the first reaction zone comprises ethylene and/or ethane for oxidation to acetic acid with the second reaction zone comprising acetic acid and ethylene with the product streams being subsequently separated thereby producing vinyl acetate. See U.S. Pat. No. 6,476,261 to Ellis et al. which describes an oxidation process for the production of alkenes and carboxylic acids such as ethylene and acetic acid which are reacted to form vinyl acetate demonstrating that more than one reaction zone can be used to form the vinyl acetate.

From the foregoing it is apparent that existing processes do not have the requisite selectivity to ethylene nor does the existing art indicate starting materials other than acetic acid which are expensive and/or intended to produce products other than ethylene.

The present invention utilizes ethylene derived from acetic acid to make VAM in an integrated process, providing alternate synthetic routes which may be utilized for more cost effective production.

SUMMARY OF THE INVENTION

It has now been unexpectedly found that VAM can be produced on an industrial scale involving an integrated process by which ethylene is produced from acetic acid with high selectivity and yield, which is converted to VAM in a subsequent step. VAM formation is referred to as "stage 2" below for convenience, while ethylene production is referred to as "stage 1". Each of these stages, especially stage 1 can be carried out in more than one reactor, if so desired, as will become apparent from the discussion which follows.

With high selectivity and yield it is now possible to produce VAM economically in two stages from acetic acid as the only C2 feedstock. Accordingly, in one embodiment of the present invention there is provided an integrated process in which acetic acid is directly converted to ethylene in a single reaction zone with the ethylene further reacted with additional acetic acid in another reaction zone to form VAM. In another embodiment of the present invention there is also provided an integrated process including hydrogenating acetic acid utilizing a first catalyst composition in a first reaction zone and dehydrating or cracking hydrogenated intermediates with a second catalyst in a second reaction zone to form ethylene with high selectivity, then reacting the ethylene in third reaction zone with acetic acid to produce VAM.

DETAILED DESCRIPTION OF INVENTION

The invention is described in detail below with reference to numerous embodiments for purposes of exemplification and illustration only. Modifications to particular embodiments within the spirit and scope of the present invention, set forth in the appended claims, will be readily apparent to those of skill in the art.

Unless more specifically defined below, terminology as used herein is given its ordinary meaning. % and like terms refer to mole percent unless otherwise indicated.

"Conversion" is expressed as a mole percentage based on acetic acid in the feed. The conversion of acetic acid (AcOH) is calculated from gas chromatography (GC) data using the following equation:

$$\text{AcOH conversion } (\%) = 100 * \frac{\text{mmol AcOH in (feed stream)} - \text{mmol AcOH out } (GC)}{\text{mmol AcOH in (feed Stream)}}$$

"Selectivity" is expressed as a mole percent based on converted acetic acid. For example, if the conversion is 50 mole % and 50 mole % of the converted acetic acid is converted to ethylene, we refer to the ethylene selectivity as 50%. Selectivity is calculated from gas chromatography (GC) data as follows:

$$\text{Ethylene Selectivity, } \% = 100 * \frac{\text{mmol Ethylene out } (GC)}{\frac{\text{Total mmol } C \text{ out } (GC)}{2} - \text{mmol AcOH out } (GC)}$$

Stage 1. Formation of Ethylene from Acetic Acid

For purposes of convenience, we refer herein to the formation of ethylene from acetic acid as "stage 1" of the inventive process whether this aspect of the process takes place in one reaction zone or a series of reaction zones as described herein.

Without intending to be bound by theory, it is believed the conversion of acetic acid to ethylene in accordance with the stage 1 of the process of this invention proceeds in accordance with one or more of the following chemical equations:

Step 1a: Hydrogenation of Acetic Acid to Ethylene.

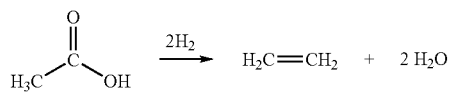

Step 1b: Hydrogenation of Acetic Acid to Ethanol.

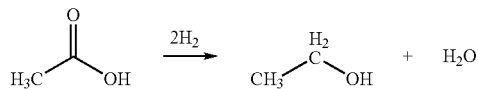

Step 1c: Hydrogenation of Acetic Acid to Ethyl Acetate.

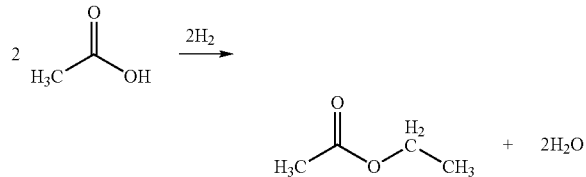

Step 2a: Cracking of Ethyl Acetate to Ethylene and Acetic Acid.

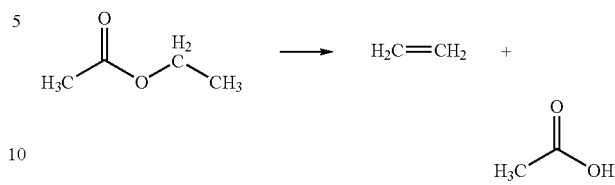

Step 2b: Dehydration of Ethanol to Ethylene.

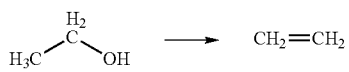

Step c: Oxidative Addition of Acetic Acid to Ethylene to Form VAM

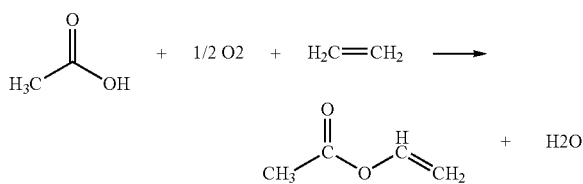

In accordance with one embodiment of the present invention regarding making ethylene for further conversion to VAM, conversion of acetic acid to ethylene is carried out in a single reaction zone which may be a single fixed bed, for example. The fixed bed can comprise a mixture of different catalyst particles or catalyst particles which include multiple catalysts. Typically, at least a hydrogenating catalyst is included in the reaction zone and optionally there is included a dehydrating and/or cracking catalyst as well.

Various hydrogenating catalysts known to one skilled in the art can be employed in hydrogenating acetic acid to ethanol in the first step of the process of this invention. The hydrogenating catalysts that are suitable are the ones which are metal catalysts on a suitable support. As noted earlier, the following catalysts may be mentioned without any limitation: copper, cobalt, ruthenium, nickel, aluminum, chromium, zinc, palladium and a mixture thereof. Typically, a single metal, a bimetallic catalyst or a trimetallic catalyst on a suitable support can be used as a hydrogenating catalyst. Thus either copper alone or in combination with aluminum, chromium or zinc are particularly preferred. Similarly, cobalt alone or in combination with ruthenium is preferred. Examples of additional metals that can be used with cobalt as a second or third metal include without any limitation the following: platinum, palladium, rhodium, rhenium, iridium, chromium, copper, tin, molybdenum, tungsten and vanadium.

Various catalyst supports known in the art can be used to support the catalysts of this invention. Examples of such supports include without any limitation, zeolite, iron oxide, silica, alumina, titania, zirconia, magnesium oxide, calcium silicate, carbon, graphite and a mixture thereof. Preferred supports are H-ZSM-5, iron oxide, silica, calcium silicate, carbon or graphite. It is also important to note that the higher the purity of silica the better it is preferred as a support in this invention.

Specific examples of supported hydrogenating catalysts include zeolite, such as H-ZSM-5, iron oxide, silica, alumina, titania, zirconia, magnesium oxide, calcium silicate, carbon, graphite and a mixture thereof. Particularly, as noted above, copper supported on iron oxide, copper-aluminum catalyst, cobalt supported on H-ZSM-5, a bimetallic catalyst ruthenium-cobalt supported on silica, cobalt supported on carbon are preferred.

A few of the commercially available catalysts include the following: copper-aluminum catalyst sold under the name of T-4489 by Sud Chemie; copper-zinc catalysts sold under the name of T-2130, T-4427 and T-4492; copper-chromium catalysts sold under the name of T-4419 and G-99B; and nickel catalysts sold under the name of NiSAT 310, C47-7-04, G-49, and G-69; all sold by Sud Chemie. Copper-aluminum catalyst sold under the name of T-4489 is particularly preferred.

The amount of metal loading on a support is not very critical in this invention and can vary in the range of about 3 weight percent to about 10 weight percent. A metal loading of about 4 weight percent to about 6 weight percent based on the weight of the support is particularly preferred. Thus for example, 4 to 6 weight percent of copper supported on iron oxide is particularly a preferred catalyst.

The metal impregnation can be carried out using any of the known methods in the art. Typically, before impregnation the supports are dried at 120° C. and shaped to particles having size distribution in the range of about 0.2 to 0.4 mm. Optionally the supports may be pressed, crushed and sieved to a desired size distribution. Any of the known methods to shape the support materials into desired size distribution can be employed.

For supports having low surface area, such as for example alpha-alumina or iron oxide, the metal solutions are added in excess until complete wetness or excess liquid impregnation so as to obtain desirable metal loadings.

As noted above, a few of the hydrogenating catalysts are bimetallic. Generally, in such cases, one metal acts as a promoter metal and the other metal is the main metal. For instance copper, nickel, cobalt and iron are considered to be main metals for preparing hydrogenating catalysts of this invention. The main metal can be combined with a promoter metal such as tungsten, vanadium, molybdenum, chromium or zinc. However, it should be noted that sometimes main metal can also act as a promoter metal or vice versa. For example, nickel can be used as a promoter metal when iron is used as a main metal. Similarly, chromium can be used as a main metal in conjunction with copper (i.e., Cu—Cr as main bimetallic metals), which can further be combined with promoter metals such as cerium, magnesium or zinc.

The bimetallic catalysts are generally impregnated in two steps. First, the "promoter" metal is added, followed by "main" metal. Each impregnation step is followed by drying and calcination. The bimetallic catalysts may also be prepared by co-impregnation. In the case of trimetallic Cu/Cr-containing catalysts as described above, a sequential impregnation may be used, starting with the addition of the "promoter" metal. The second impregnation step may involve co-impregnation of the two principal metals, i.e., Cu and Cr. For example, Cu—Cr—Ce on $SiO_2$ may be prepared by a first impregnation of cerium nitrate, followed by the co-impregnation of copper and chromium nitrates. Again, each impregnation is followed by drying and calcinations. In most cases, the impregnation may be carried out using metal nitrate solutions. However, various other soluble salts which upon calcination releases metal ions can also be used. Examples of other suitable metal salts for impregnation include metal hydroxide, metal oxide, metal acetate, ammonium metal oxide, such as ammonium heptamolybdate hexahydrate, metal acids, such as perrhenic acid solution, metal oxalate, and the like.

As already noted above, any of the known zeolites can be used as support catalysts. A wide variety of zeolite catalysts are known in the art including synthetic as well as natural, all of which can be used as support catalysts in this invention. More particularly, any zeolite having a pore diameter of at least about 0.6 nm can be used, preferably employed among such zeolites are the catalysts selected from the group consisting of mordenites, ZSM-5, a zeolite X and a zeolite Y.

The preparation of large-pore mordenites is described, for example, in U.S. Pat. No. 4,018,514 to Plummer and in Mol. Sieves. Pap. Conf., 1967, 78, Soc. Chem. Ind. London, by D. DOMINE and J. QUOBEX.

Zeolite X is described, for example, U.S. Pat. No. 2,882,244 to MIlton and zeolite Y in U.S. Pat. No. 3,130,007 to Breck.

Various zeolites and zeolite-type materials are known in the art for the catalysis of chemical reactions. For example, U.S. Pat. No. 3,702,886, to Argauer, discloses a class of synthetic zeolites, characterized as "Zeolite ZSM-5", which are effective for the catalysis of various hydrocarbon conversion processes.

The zeolites suitable for the procedure of the invention can be in the basic form, in the partially or totally acidified form, or in the partially dealuminated form.

In another aspect, any known dehydration catalysts can be employed in the reaction zone of the process of this invention. Typically, a zeolite catalyst is employed as a dehydration catalyst and may support a dehydrogenating catalyst. While any zeolite having a pore diameter of at least about 0.6 nm can be used, preferably employed among such zeolites are the dehydration catalyst selected from the group consisting of mordenites, ZSM-5, a zeolite X and a zeolite Y.

An active dehydrating catalyst, characterized as "H-ZSM-5" or "H-mordenite" zeolites are prepared from a corresponding "ZSM-5" zeolite or "mordenite" zeolite by replacing most, and generally at least about 80% of the cations of the latter zeolite with hydrogen ions using techniques well-known in the art. H-mordenite zeolite, for example, was prepared by calcination of ammonium form mordenite at 500-550° C. for 4-8 hours. If the sodium form of mordenite is used as a precursor, the sodium mordenite is ion-exchanged to ammonium form prior to calcination.

These zeolite catalysts are essentially crystalline aluminosilicates or in the neutral form a combination of silica and alumina in a well defined crystalline structure. In a particularly preferred class of zeolite catalysts for purposes of the present invention, the molar ratio of $SiO_2$ to $Al_2O_3$ in these zeolites is within the ratio of about 10 to 60.

As noted earlier, ethylene is produced by dehydration as well as the decomposition or "cracking" of ethyl acetate to ethylene and acetic acid. This may simply occur as thermal cracking at elevated temperatures or may be a catalyzed reaction if so desired, utilizing a cracking catalyst. Suitable cracking catalysts include sulfonic acid resins such as perfluoro-sulfonic acid resins disclosed in U.S. Pat. No. 4,399,305 to Schreck noted above, the disclosure of which is incorporated by reference. Zeolites are also suitable as cracking catalysts as noted in U.S. Pat. No. 4,620,050 to Cognion et al., the disclosure of which is also incorporated by reference. Thus, a zeolite catalyst may be used to concurrently dehydrate ethanol to ethylene and decompose ethyl acetate to ethylene in a highly efficient process of the invention.

Selectivities of acetic acid to ethylene are suitably more than 10% and more such as at least 20%, at or least 25% or so up to about 40% in typical cases. Depending on the by-product mix, it may be desirable to operate at intermediate selectivities, and recirculate products such as acetaldehyde for further hydrogenating and dehydration provided selectivity to undesirable products such as $CO_2$ remains low.

Preferably, for the purposes of the process of this invention, the suitable hydrogenating catalyst is either copper on iron oxide or copper-aluminum catalyst, sold under the tradename of T-4489 by Sud Chemie, cobalt supported on H-ZSM-5, a bimetallic catalyst, ruthenium and cobalt supported on silica, and cobalt supported on carbon. In this embodiment of the process of this invention, the copper loading on the iron oxide support or in the bimetallic copper-aluminum catalyst is typically in the range of about 3 weight percent to about 10 weight percent, preferably it is in the range of about 4 weight percent to about 6 weight percent. Similarly, the loading of cobalt on H-ZSM-5 or silica or carbon is typically around 5 weight percent. The amount of ruthenium in the bimetallic catalyst is also around 5 weight percent.

In addition, the acetic acid hydrogenation and dehydration are carried out at a pressure just sufficient to overcome the pressure drop across the catalytic bed.

The reaction may be carried out in the vapor or liquid state under a wide variety of conditions. Preferably, the reaction is carried out in the vapor phase. Reaction temperatures may be employed, for example in the range of about 200° C. to about 375° C., preferably about 250° C. to about 350° C. The pressure is generally uncritical to the reaction and subatmospheric, atmospheric or superatmospheric pressures may be employed. In most cases, however, the pressure of the reaction will be in the range of about 1 to 30 atmospheres absolute.

Although the reaction consumes two moles of hydrogen per mole of acetic acid to produce a mole of ethylene, the actual molar ratio of acetic acid to hydrogen in the feed stream may be varied between wide limits, e.g. from about 100:1 to 1:100. It is preferred however that such ratio be in the range of about 1:20 to 1:2.

It is well known to produce acetic acid through methanol carbonylation, acetaldehyde oxidation, ethylene oxidation, oxidative fermentation, and anaerobic fermentation and so forth. As petroleum and natural gas have become more expensive, methods for producing acetic acid and intermediates such as methanol and carbon monoxide from alternate carbon sources have drawn more interest.

Of particular interest is the production of acetic acid from synthesis gas (syngas) that may be derived from any suitable carbon source. U.S. Pat. No. 6,232,352 to Vidalin, the disclosure of which is incorporated herein by reference, for example, teaches a method of retrofitting a methanol plant for the manufacture of acetic acid. By retrofitting a methanol plant the large capital costs associated with CO generation for a new acetic acid plant are significantly reduced or largely eliminated. All or part of the syngas is diverted from the methanol synthesis loop and supplied to a separator unit to recover CO and hydrogen, which are then used to produce acetic acid. In addition to acetic acid, the process can also be used to make hydrogen which is utilized in connection with this invention.

U.S. Pat. No. RE 35,377 to Steinberg et al., also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syngas is converted to methanol which may be carbonylated to acetic acid. The method likewise produces hydrogen which may be used in connection with this invention as noted above. See also, U.S. Pat. No. 5,821,111 to Grady et al., which discloses a process for converting waste biomass through gasification into synthesis gas as well as U.S. Pat. No. 6,685,754 to Kindig et al., the disclosures of which are incorporated herein by reference.

The acetic acid may be vaporized at the reaction temperature, and then it can be fed along with hydrogen in an undiluted state or diluted state with a relatively inert carrier gas, such as nitrogen, argon, helium, carbon dioxide and the like.

Alternatively, acetic acid in vapor form may be taken directly as crude product from the flash vessel of a methanol carbonylation unit of the class described in U.S. Pat. No. 6,657,078 to Scates et al., the disclosure of which is incorporated by reference. The crude vapor product may be fed directly to the reaction zones of the present invention without the need for condensing the acetic acid and light ends or removing water, saving overall processing costs.

Contact or residence time can also vary widely, depending upon such variables as the amount of acetic acid, catalyst, reactor, temperature and pressure. Typical contact times range from a fraction of a second to more than several hours when a catalyst system other than a fixed bed is used, with preferred contact times, at least for vapor phase reactions, between about 0.5 and 100 seconds.

Typically, the catalyst is employed in a fixed bed reactor e.g. in the shape of an elongated pipe or tube where the reactants, typically in the vapor form, are passed over or through the catalyst. Other reactors, such as fluid or ebullient bed reactors, can be employed, if desired. In some instances, it is advantageous to use the catalyst bed in conjunction with an inert material such as glass wool to regulate the pressure drop of the reactant stream through the catalyst bed and the contact time of the reactant compounds with the catalyst particles.

In one of the examples there is provided a process for selective formation of ethylene from acetic acid comprising: contacting a feed stream of acetic acid and hydrogen at a temperature in the range of about 250° C. to 350° C. with a catalyst chosen from copper supported on iron oxide, copper-aluminum catalyst, cobalt supported on H-ZSM-5, ruthenium-cobalt supported on silica or cobalt supported on carbon to form ethylene.

In one of the examples, the preferred catalyst is 5 weight percent copper on iron oxide, 5 weight percent cobalt on H-ZSM-5, 5 weight percent cobalt and 5 weight percent ruthenium on silica or 5 weight percent cobalt on carbon. In this embodiment of the process of this invention it is preferred that the reaction is carried out in the vapor phase in a tubular reactor packed with the catalyst bed and at a temperature in the range of about 250° C. to 350° C. and at a pressure in the range of about 1 to 30 atmospheres absolute, and the contact time of reactants is in the range of about 0.5 and 100 seconds.

Stage 2. Formation of VAM from the Gaseous Product Stream Containing Ethylene and Additional Amounts of Acetic Acid As noted earlier, for purposes of convenience we refer to the reaction of the ethylene formed in stage 1 with additional acetic acid and oxygen to form VAM as "stage 2" of the inventive process herein, whether or not more than 2 specific process steps are involved in the conversion.

In a second (or third depending upon the process parameters used for the formation of product stream containing ethylene) reactor zone the gaseous product stream from the hydrogenating reactor is contacted further with a catalyst and a second feed containing molecular oxygen and additional amounts of acetic acid. It is preferable that equal mole ratios of ethylene and acetic acid are fed into this reactor zone.

Any of the known catalysts for oxidative reaction of ethylene with acetic acid to form VAM can be employed in stage 2 of the process of this invention, for example, as described in GB 1 559 540, U.S. Pat. Nos. 5,185,308; 5,691,267; 6,114,571; and WO 99/08791 the equivalent to U.S. Pat. No. 6,603,038. EP-A 0 330 853 describes impregnated catalysts for the production of VAM containing palladium, potassium, manganese and cadmium as additional promoter instead of gold. See also, U.S. Pat. No. 6,852,877. All of the references mentioned immediately above are incorporated herein by reference in their entirety as relating to forming VAM from ethylene, acetic acid and oxygen.

GB 1 559 540 describes suitable catalysts that can be employed in the preparation of VAM by the reaction of ethylene, acetic acid and oxygen, as used in step (d) of the process of this invention. The catalyst is comprised of: (1) a catalyst support having a particle diameter of from 3 to 7 mm and a pore volume of from about 0.2 to 1.5 ml/g, a 10% by weight water suspension of the catalyst support having a pH from about 3.0 to 9.0, (2) a palladium-gold alloy distributed in a surface layer of the catalyst support, the surface layer extending less than 0.5 mm from the surface of the support, the palladium in the alloy being present in an amount of from about 1.5 to 5.0 grams per liter of catalyst, and the gold being present in an amount of from about 0.5 to 2.25 grams per liter of catalyst, and (3) from 5 to 60 grams per liter of catalyst of alkali metal acetate.

U.S. Pat. No. 5,185,308 to Bartley et al. describes a shell impregnated catalyst active for the production of VAM from ethylene, acetic acid and an oxygen containing gas, the catalyst consisting essentially of (1) a catalyst support having a particle diameter from about 3 to about 7 mm and a pore volume of 0.2 to 1.5 ml per gram, (2) palladium and gold distributed in the outermost 1.0 mm thick layer of the catalyst support particles, and (3) from about 3.5 to about 9.5% by weight of potassium acetate wherein the gold to palladium weight ratio in said catalyst is in the range 0.6 to 1.25.

U.S. Pat. No. 5,691,267 to Nicolau et al. describes a two step gold addition method for a catalyst used in the gas phase formation of VAM from the reaction of ethylene, oxygen, and acetic acid. The catalyst is formed by (1) impregnating a catalyst carrier with aqueous solutions of a water-soluble palladium salt and a first amount of a water-soluble gold compound such as sodium-palladium chloride and auric chloride, (2) fixing the precious metals on the carrier by precipitating the water-insoluble palladium and gold compounds by treatment of the impregnated carriers with a reactive basic solution such as aqueous sodium hydroxide which reacts with the palladium and gold compounds to form hydroxides of palladium and gold on the carrier surface, (3) washing with water to remove the chloride ion (or other anion), and (4) reducing all the precious metal hydroxides to free palladium and gold, wherein the improvement comprises (5) impregnating the carrier with a second amount of a water-soluble gold compound subsequent to fixing a first amount of water-soluble gold agent, and (6) fixing the second amount of a water-soluble gold compound.

U.S. Pat. No. 6,114,571 to Abel et al. describes a catalyst for forming vinyl acetate in the gas phase from ethylene, acetic acid, and oxygen or oxygen-containing gases wherein the catalyst is comprised of palladium, gold, boron, and alkali metal compounds on a support. The catalyst is prepared by a) impregnating the support with soluble palladium and gold compounds; b) converting the soluble palladium and gold compounds on the support into insoluble compounds by means of an alkaline solution; c) reducing the insoluble palladium and gold compounds on the support by means of a reducing agent in the liquid phase; d) washing and subsequently drying the support; e) impregnating the support with a soluble alkali metal compound; and f) finally drying the support at a maximum of 1500 c., wherein boron or boron compounds are applied to the catalyst prior to the final drying.

WO 99/08791, the equivalent to U.S. Pat. No. 6,603,038 to Hagemeyer et al., describes a method for producing catalysts containing metal nanoparticles on a porous support, especially for gas phase oxidation of ethylene and acetic acid to form VAM. The invention relates to a method for producing a catalyst containing one or several metals from the group of metals comprising the sub-groups Ib and VIIb of the periodic table on porous support particles, characterized by a first step in which one or several precursors from the group of compounds of metals from sub-groups Ib and VIIb of the periodic table is or are applied to a porous support, and a second step in which the porous, preferably nanoporous support to which at least one precursor has been applied is treated with at least one reduction agent, to obtain the metal nanoparticles produced in situ in the pores of said support.

Typically, VAM formation of the process of the present invention is carried out heterogeneously with the reactants being present in the gas phase.

The molecular oxygen-containing gas used in formation of VAM in the process of the present invention may comprise other inert gases such as nitrogen. Preferably molecular oxygen used in forming VAM is air.

Stage 2 of the process of the present invention may suitably be carried out at a temperature in the range of from about 140° C. to 220° C. Stage 2 of the process of the present invention may suitably be carried out at a pressure in the range of from about 1 to 100 atmospheres absolute. Stage 2 of the process of the present invention can be carried out in any suitable reactor design capable of removing the heat of reaction in an appropriate way; preferred technical solutions are fixed or fluidized bed reactors as described herein.

Acetic acid conversions in the range of about 5 to 50% may be achieved in stage 2 of the process of the present invention. Oxygen conversions in the range of about 20 to 100% may be achieved in stage 2 of the present invention. In stage 2 of the process of the present invention, the catalyst suitably has a productivity (space time yield, STY) in the range of about 100 to 2000 grams of vinyl acetate per hour per liter of catalyst, but >10000 grams of vinyl acetate per hour per liter of catalyst is also suitable.

As already noted above, the gaseous product stream from stage 2 of the process comprises VAM and water and optionally also unreacted acetic acid, ethylene, ethyl acetate, ethane, nitrogen, carbon monoxide, carbon dioxide and possibly traces of other byproducts. Intermediate between stage 2 and VAM separation step of the process of the invention it is preferred to remove ethylene, and ethane, carbon monoxide and carbon dioxide, if any, from the product stream, suitably as an overhead gaseous fraction from a scrubbing column, in which a liquid fraction comprising vinyl acetate, water and acetic acid is removed from the base.

The product stream from stage 2 comprising VAM, water and acetic acid, with or without the intermediate scrubbing step, is separated in the final step by distillation into an overhead azeotrope fraction comprising vinyl acetate and water and a base fraction comprising acetic acid.

VAM is recovered from the azeotrope fraction separated in stage 2 process step of the invention, suitably for example by decantation. The recovered VAM may, if desired, be further purified in known manner. The base fraction comprising acetic acid separated in stage 2 is preferably recycled, with or preferably without further purification, to stage 1 or, if desired, to stage 2 of the process.

The following examples describe the procedures used for the preparation of various catalysts employed in the process of this invention.

EXAMPLE A

Preparation of 5 Weight Percent Copper on Iron Oxide

Powdered and meshed iron oxide (95 g) of uniform particle size distribution of about 0.2 mm was dried at 120° C. in an oven under nitrogen atmosphere overnight and then cooled to room temperature. To this was added a solution of copper nitrate (17 g) in distilled water (100 ml). The resulting slurry was dried in an oven gradually heated to 110° C. (>2 hours, 10° C./min.). The impregnated catalyst mixture was then calcined at 500° C. (6 hours, 1° C./min).

EXAMPLE B

Preparation of H-Mordenite Zeolite

H-Mordenite zeolite was prepared by calcination of ammonium form Mordenite at 500-550° C. for 4-8 hours. If the sodium form of Mordenite is used as a precursor, the sodium Mordenite is ion-exchanged to ammonium form prior to calcination.

EXAMPLE C

Preparation of 5 Weight Percent Cobalt on H-ZSM-5

Example A is substantially repeated with the exception of using appropriate amount of cobalt nitrate hexahydrate as the metal salt and H-ZSM-5 as the support catalyst to prepare 5 weight percent cobalt supported on H-ZSM-5.

EXAMPLE D

Preparation of 5 Weight Percent Cobalt and 5 Weight Percent Ruthenium on Silica

Example A is substantially repeated with the exception of using appropriate amounts of cobalt nitrate hexahydrate and ruthenium nitrosyl nitrate as the metal salts and silica as the support catalyst to prepare 5 weight percent cobalt and 5 weight percent ruthenium supported on silica.

EXAMPLE E

Preparation of 5 Weight Percent Cobalt on Carbon

Example A is substantially repeated with the exception of using appropriate amount of cobalt nitrate hexahydrate as the metal salt and carbon as the support catalyst to prepare 5 weight percent cobalt supported on carbon.

EXAMPLE F

K, Pd, Au/TiO$_2$ catalyst for converting ethylene, acetic acid and oxygen to VAM is prepared generally as follows:

2.11 g palladium acetate (Aldrich) and 1.32 g gold acetate is dissolved in 30 ml acetic acid. The preparation of the employed gold acetate is described e.g., in U.S. Pat. No. 4,933,204 to Warren, Jr. et al. 100 ml TiO$_2$ support (P25 pellets, Degussa, Hanau) are added to the palladium and gold acetate solution. Then, the majority of acetic acid is evaporated using a rotary evaporator at 70° C., followed by evaporating the rest using an oil pump at 60° C. and finally in a vacuum drying cabinet at 60° C. for 14 h.

The resulting pellets are reduced with a gas mixture of 10 vol % hydrogen in nitrogen, while passing the gas (40 l/h) directly through the pellets at 500° C. and 1 bar for 1 h. For loading with potassium ions, the reduced pellets are added to a solution containing 4 g potassium acetate in 30 ml of water, for 15 minutes in a mixing apparatus.

Then, the solvent is evaporated using a rotary evaporator. The pellets are dried at 100° C. for 14 h.

EXAMPLE G

Preparation of Pd and Au

A vinyl acetate catalyst containing Pd and Au for converting a stream of gas containing ethylene, oxygen or air, and acetic acid into VAM is prepared generally as follows:

the catalyst is prepared on spherical silica supports with diameters of about 5 mm (SudChemie). The silica supports are impregnated with an aqueous solution containing sodium palladium tetrachlorate and sodium tetracholroaurate in sufficient amounts such that the catalysts would have about 7 gm/l of palladium metal and about 7 gm/l of gold metal each.

After impregnation, the carrier is placed in a roto-evaporator, without vacuum, and treated with 283 ml of a 50% w/w aqueous solution of sodium hydroxide. The supports are rotated at about 5 rpm for about 2.5 hours in a sodium hydroxide solution at a temperature of 70° C. by rotation in a hot water bath. The resulting catalysts are reduced in a gas blend of 5% ethylene in nitrogen for about 5 hours at a temperature of about 150° C. at a flow rate of about 0.5 SCFH (standard cubic feet per hour) at atmospheric pressure to reduce the metal salts to metal.

The catalysts are then impregnated again with an aqueous solution of sodium tetrachloroaurate and 1.65 gm of a 50% w/w aqueous sodium hydroxide fixing solution. The resulting catalysts are reduced in a gas blend of 5% ethylene in nitrogen for about 5 hours at a temperature of about 150° C. at a flow rate of about 0.5 SCFH (standard cubic feet per hour) at atmospheric pressure to reduce the gold salts to gold metal.

EXAMPLE H

Preparation of Pd, Au, and K

A catalyst for preparing vinyl acetate in the gas phase from ethylene, acetic acid, and oxygen or oxygen-containing gases wherein the catalyst is prepared generally as follows:

250 ml of silicon dioxide catalyst sphere supports having a diameter of 7.3 mm (Sud Chemie) were impregnated with 85 ml of an aqueous solution containing 4.6 g of Na$_2$PdCl$_4$ and 1.4 g of NaAuCl$_4$. The precipitation of the insoluble metal compounds is achieved by the addition of 283 ml of an aqueous solution of 17 g of borax. The vessel is then immediately rotated by means of a rotary evaporator without vacuum, for 2.5 hours at 5 revolutions per minute (rpm). The reduction is achieved by the addition of 7 ml of hydrazine hydrate in 20 ml of water and immediate rotation of the vessel at 5 rpm for 1 hour.

The pellets thus obtained were dried for 1 hour at 1000 C. The reduced catalyst is impregnated with an aqueous solution containing 10 g of potassium acetate and having a volume corresponding to the absorption capacity of the dry support material. The catalyst is then dried again.

EXAMPLE I

Preparation of Pd, Au, and B

A catalyst containing nanosize metal particles on a porous support for the gas phase oxidation of ethylene and acetic acid to give vinyl acetate is prepared as follows:

200 g of SiO2 supports (Siliperl AF125, Engelhard) having a BET surface area of 300 m$^2$/g were sprayed discontinuously at a temperature of 30-32° C. with a hydro-chloric acid solution of 3.33 g (18.8 mmol) of palladium chloride and 1.85 g (4.7 mmol) of auric acid in 500 ml of water over a period of 35 minutes in a coating unit.

The support spheres were subsequently dried and sprayed with 20 g of tripotassium citrate hydrate dissolved in 200 ml of water over a period of 25 minutes. At a drum rotation speed of 10 rpm, spraying is carried out discontinuously at 1 bar. The inlet temperature (warm air temperature) is 60° C. and the product temperature is 32-30° C. This gave a homogeneously impregnated coated catalyst having a shell thickness of 400 μm. The diameter of the nanosize particles is determined by means of TEM. The mean particle diameter is 30 nm.

Gas Chromatographic (GC) Analysis of the Products

The analysis of the products is carried out by online GC. A three channel compact GC equipped with one flame ionization detector (FID) and 2 thermal conducting detectors (TCDs) is used to analyze the reactants and products. The front channel was equipped with an FID and a CP-Sil 5 (20 m)+WaxFFap (5 m) column and was used to quantify:

Acetaldehyde
Ethanol
Acetone
Methyl acetate
Vinyl acetate
Ethyl acetate
Acetic acid
Ethylene glycol diacetate
Ethylene glycol
Ethylidene Diacetate
Paraldehyde The middle channel was equipped with a TCD and Porabond Q column and was used to quantify:

$CO_2$
Ethylene
Ethane

The back channel was equipped with a TCD and Molsieve 5A column and was used to quantify:

Helium
Hydrogen
Nitrogen
Methane
Carbon monoxide

Prior to reactions, the retention time of the different components was determined by spiking with individual compounds and the GCs were calibrated either with a calibration gas of known composition or with liquid solutions of known compositions. This allowed the determination of the response factors for the various components.

Examples 1 and 2 illustrate the formation of ethylene in a dual reaction zone using two catalysts, hydrogenation and dehydration catalysts, in the stage 1 of the process of this invention.

EXAMPLE 1

The catalysts utilized were a copper on iron oxide catalyst, T-4489 purchased from Sud Chemie and an H-mordenite zeolite prepared by replacing with hydrogen ions all but 500 ppm based on the weight of the zeolite of the sodium ions in a sodium aluminosilicate mordenite catalyst prepared in accordance with U.S. Pat. No. 4,018,514 to Plummer or equivalent in which the ratio of silica to alumina is preferably in the range of from about 15:1 to about 100:1. A suitable catalyst is CBV21A available from Zeolyst International, which has a silica to alumina ratio of about 20:1.

In a tubular reactor made of stainless steel, having an internal diameter of 30 mm and capable of being raised to a controlled temperature, there are arranged 30 ml of 5 weight percent copper on iron oxide catalyst as top layer and 20 ml of H-mordenite as a bottom layer. The length of the combined catalyst bed after charging was approximately about 70 mm.

A feed liquid was composed essentially of acetic acid. The reaction feed liquid was evaporated and charged to the reactor along with hydrogen and helium as a carrier gas with an average combined gas hourly space velocity (GHSV) of 2500 hr$^{-1}$ at a temperature of 300° C. and pressure of 100 psig. The feed stream contained a mole percent of acetic acid from about 6.1% to about 7.3% and mole percent of hydrogen from about 54.3% to about 61.5%. The feed stream was supplied to the hydrogenation catalyst (top) layer first such that the stream with hydrogenated acetic acid intermediates then contacted the dehydration catalyst layer. A portion of the vapor effluent from the reactor was passed through a gas chromatograph for analysis of the contents of the effluents. The acetic acid conversion was 65% and ethylene selectivity was 85%. Selectivity to acetone was 3%, selectivity to ethyl acetate was 2% and selectivity to ethanol was 0.6%. Carbon dioxide was relatively low; the measured selectivity to $CO_2$ of the acetic acid converted was 4%.

EXAMPLE 2

The catalysts utilized were 5 weight percent copper on iron oxide prepared in accordance with the procedure of Example A and an H-mordenite zeolite prepared by replacing with hydrogen ions all but 500 ppm based on the weight of the zeolite of the sodium ions in a sodium aluminosilicate mordenite catalyst as noted above in Example 1.

The procedure as set forth in Example 1 was substantially repeated with an average combined gas hourly space velocity (GHSV) of 2500 hr$^{-1}$ of the feed stream of vaporized acetic acid, hydrogen and helium at a temperature of 350° C. and pressure of 100 psig. The resulting feed stream contained a mole percent of acetic acid of about 7.3% and mole percent of hydrogen of about 54.3%. A portion of the vapor effluent was passed through a gas chromatograph for analysis of the contents of the effluents. The acetic acid conversion was 8% and ethylene selectivity was 18%.

Generally speaking, selectivities to ethylene above 10% or so are highly desirable; it being appreciated that the other by-products such as ethanol or ethyl acetate can be re-cycled to the reactor along with unreacted acetic acid, while still other by-products can be re-processed or used for fuel value. Selectivities to $CO_2$ of less than 10% are desired, preferably less than 5%.

COMPARATIVE EXAMPLES 1A-5A

These examples illustrate the reaction of acetic acid and hydrogen over a variety of catalysts wherein either no ethylene was formed and/or very low levels of ethylene was detected.

In all of these examples the procedure as set forth in Example 1 was substantially followed with the exception of using different catalysts as listed in Table 1. As summarized in Table 1, in all of these comparative examples only one single layer of catalyst was used. The reaction temperature and selectivity to ethylene are also tabulated in Table 1.

TABLE 1

| Reactor Bed | Catalyst | Reactor Temperature (° C.) | Mol % H$_2$ in Feed Stream | Mol % Acetic Acid in Feed Stream | Ethylene Selectivity |
|---|---|---|---|---|---|
| Single Layer | 0.5%-1% Pd on Carbon | 250-350° C. | 54.2% | 7.3% | 0% |
| Single Layer | 1% Ru on Carbon | 250-350° C. | 36.8% | 7.3% | 0% |
| Single Layer | 2% Pt on Fe$_2$O$_3$ | 350° C. | 34.3%-76.5% | 4.4%-7.3% | 0%-1% |
| Single Layer | 2.58% Pd/ 5.05% Mo on SiO$_2$ | 250-350° C. | 36.8% | 7.3% | 0%-0.5% |
| Single Layer | 4.79% Cu on SiO2 | 400° C. | 35.2% | 7.5% | 0%-2.25% |

In these examples various other products including acetaldehyde, ethanol, ethyl acetate, ethane, carbon monoxide, carbon dioxide, methane, isopropanol, acetone and water were detected.

Examples 3-6 illustrate formation of ethylene in a single reactor in the Stage 1 of the process of this invention.

EXAMPLE 3

The catalyst utilized was 5 weight percent copper on iron oxide prepared in accordance with the procedure of Example A.

In a tubular reactor made of stainless steel, having an internal diameter of 30 mm and capable of being raised to a controlled temperature, there are arranged 50 ml of 5 weight percent copper on iron oxide catalyst. The length of the catalyst bed after charging was approximately about 70 mm.

A feed liquid was composed essentially of acetic acid. The reaction feed liquid was evaporated and charged to the reactor along with hydrogen and helium as a carrier gas with an average combined gas hourly space velocity (GHSV) of about 2500 hr$^{-1}$ at a temperature of about 350° C. and pressure of 100 psig. The resulting feed stream contained a mole percent of acetic acid from about 4.4% to about 13.8% and the mole percent of hydrogen from about 14% to about 77%. A portion of the vapor effluent was passed through a gas chromatograph for analysis of the contents of the effluents. Results appear in Table 2. The selectivity to ethylene was 16% at an acetic acid conversion of 100%

EXAMPLE 4

The catalyst utilized was 5 weight percent cobalt on H-ZSM-5 prepared in accordance with the procedure of Example C.

The procedure as set forth in Example 3 was substantially repeated with an average combined gas hourly space velocity (GHSV) of 10,000 hr$^{-1}$ of the feed stream of the vaporized acetic acid, hydrogen and helium at a temperature of 250° C. and pressure of 1 bar. A portion of the vapor effluent was passed through a gas chromatograph for analysis of the contents of the effluents. Results appear in Table 2. The acetic acid conversion was 3% and ethylene selectivity was 28%.

EXAMPLE 5

The catalyst utilized was a bimetallic catalyst containing 5 weight percent cobalt and 5 weight percent ruthenium supported on silica prepared in accordance with the procedure of Example D.

The procedure as set forth in Example 1 was substantially repeated with an average combined gas hourly space velocity (GHSV) of 2500 hr$^{-1}$ of the feed stream of the vaporized acetic acid, hydrogen and helium at a temperature of 350° C. and pressure of 1 bar. A portion of the vapor effluent was passed through a gas chromatograph for analysis of the contents of the effluents. Results appear in Table 2. The acetic acid conversion was 4% and ethylene selectivity was 14%.

EXAMPLE 6

The catalyst utilized was 5 weight percent cobalt supported on carbon prepared in accordance with the procedure of Example E.

The procedure as set forth in Example 1 was substantially repeated with an average combined gas hourly space velocity (GHSV) of 2500 hr$^{-1}$ of the feed stream of the vaporized acetic acid, hydrogen and helium at a temperature of 350° C. and pressure of 1 bar. A portion of the vapor effluent was passed through a gas chromatograph for analysis of the contents of the effluents. Results appear in Table 2. The acetic acid conversion was 2% and ethylene selectivity was 12%.

Generally speaking, selectivities to ethylene above 10% or so are highly desirable; it being appreciated that the other by-products such as ethanol or ethyl acetate can be re-cycled to the reactor along with unreacted acetic acid, while still other by-products can be re-processed or used for fuel value. Selectivities to $CO_2$ of less than 10% are desired, preferably 5% or less.

TABLE 2

Acetic Acid Conversion and Selectivities

| Example | Ethylene selectivity (%) | Acetic acid conversion (%) | Other products |
|---|---|---|---|
| 3 | 16 | 100 | acetaldehyde-31%, ethane-15%, ethyl acetate-4%, $CO_2$-5% |
| 4 | 29 | 3 | acetaldehyde-51%, ethane-28% |
| 5 | 14 | 4 | acetaldehyde-78%, ethane-8% |
| 6 | 12 | 2 | acetone-8%, methane-47%, ethane-5% |

COMPARATIVE EXAMPLES 6A-10A

These examples illustrate the reaction of acetic acid and hydrogen over a variety of catalysts wherein either no ethylene was formed and/or very low levels of ethylene was detected.

In all of these examples the procedure as set forth in Example 3 was substantially followed with the exception of using different catalysts as listed in Table 3. The reaction temperature and selectivity to ethylene are also tabulated in Table 3.

TABLE 3

| Catalyst | Reactor Temperature (° C.) | Mol % $H_2$ In Feed | Mol % Acetic Acid In Feed | Ethylene Selectivity |
|---|---|---|---|---|
| 0.5%-1% Pd on Carbon | 250-350° C. | 54.2% | 7.3% | 0% |
| 1% Ru on Carbon | 250-350° C. | 36.8% | 7.3% | 0% |
| 2% Pt on $Fe_2O_3$ | 350° C. | 34.3%-76.5% | 4.4%-7.3% | 0%-1% |
| 2.58% Pd/5.05% Mo on $SiO_2$ | 250-350° C. | 36.8% | 7.3% | 0%-0.5% |
| 4.79% Cu on SiO2 | 400° C. | 35.2% | 7.5% | 0%-2.25% |

In these examples various other products including acetaldehyde, ethanol, ethyl acetate, ethane, carbon monoxide, carbon dioxide, methane, isopropanol, acetone and water were detected.

EXAMPLE 7

The catalyst utilized to convert ethylene, acetic acid and oxygen to VAM is K, Pd, Au/$TiO_2$ prepared in accordance with the procedure of Example F above. The procedure as set forth in U.S. Pat. No. 6,852,877 to Zeyss et al. is used to carry out stage 2 of the process of the present invention using one of the feed streams from Examples 1-6, stage 1 of the process of the present invention and molecular oxygen in combination with stoichiometric amounts of acetic acid.

Typical reaction conditions and selectivities for stage 2 are as set forth in Table 4 below.

TABLE 4

Vinyl Acetate Synthesis

| Reaction Conditions | | Results | |
|---|---|---|---|
| T [° C.] | P [bar] | S (VAM) [%] | STY [g/(h)] |
| 155 | 9 | 98 | 1000 |
| 160 | 9 | 98 | 1050 |
| 170 | 9 | 96 | 1000 |
| 160 | 9 | 98 | 1350 |
| 170 | 9 | 97 | 700 |
| 170 | 9 | 98 | 1300 |

EXAMPLE 8

A catalyst utilized to convert ethylene, oxygen, and acetic acid to VAM is Pd/Au prepared in accordance with the procedure of Example G above. The procedure as set forth in U.S. Pat. No. 5,691,267 to Nicolau et al. is used to carry out stage 2 of the process of the present invention using one of the feed streams from Examples 1-6, stage 1 of the process of the present invention, and molecular oxygen in combination with stoichiometric amounts of acetic acid.

EXAMPLE 9

A catalyst utilized to convert ethylene, oxygen, and acetic acid to VAM is Pd/Au and boron prepared in accordance with the procedure of Example H above. The procedure as set forth in U.S. Pat. No. 6,114,571 to Abel et al. is used to carry out stage 2 of the process of the present invention using one of the feed streams from Examples 1-6, stage 1 of the process of the present invention, and molecular oxygen in combination with stoichiometric amounts of acetic acid.

EXAMPLE 10

A catalyst utilized to convert ethylene, oxygen, and acetic acid to VAM has metal containing nanoparticles on a porous support prepared in accordance with the procedure of Example I above. The procedure as set forth in U.S. Pat. No. 6,603,038 to Hagemeyer et al. is used to carry out stage 2 of the process of the present invention using one of the feed streams from Examples 1-6, stage 1 of the process of the present invention.

While it is known to react acetic acid with ethylene in order to produce VAM. It has now been unexpectedly found that ethylene can be made on an industrial scale directly from acetic acid with high selectivity and yield. As demonstrated from the Examples above, ethylene can be economically manufactured cost effectively in order to produce VAM and other products made from ethylene.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference, further description is deemed unnecessary.

What is claimed is:

1. A process for the production of vinyl acetate from acetic acid comprising:
   a. contacting in a first reaction zone a feed stream containing acetic acid and hydrogen at an elevated temperature with a suitable hydrogenating catalyst, which is effective to hydrogenate acetic acid to ethylene, said hydrogenation catalyst being selected from the group consisting of copper supported on iron oxide, cobalt supported on H-ZSM-5, copper-aluminum catalyst, copper-zinc catalyst, copper-chromium catalyst, and nickel catalyst to form a first gaseous product stream comprising ethylene, wherein the conversion of acetic acid to ethylene is at least 10%;
   b. enriching said first gaseous product stream with ethylene at least up to 50 percent;
   c. contacting in a second reaction zone said enriched first gaseous product stream obtained in step (b) in combination with a second feed stream comprising acetic acid and molecular oxygen in the presence of a catalyst to form a second gaseous product stream comprising vinyl acetate; and
   d. separating the vinyl acetate from said second gaseous product stream.

2. The process according to claim 1, wherein the hydrogenating catalyst comprises copper supported on iron oxide.

3. The process according to claim 1, wherein the first gaseous product stream is enriched with ethylene at least up to 80 percent.

4. The process according to claim 1, wherein the reactants in step (a) consist of acetic acid and hydrogen with a molar ratio in the range of about 100:1 to 1:100, the temperature of the reaction zones are in the range of about 250° C. to 350° C., and the pressure of the reaction zones are in the range of about 1 to 30 atmospheres absolute.

5. The process according to claim 1, wherein the reactants in step (a) consist of acetic acid and hydrogen with a molar ratio in the range of about 1:20 to 1:2 the temperature of the reaction zones are in the range of about 300° C. to 350° C., and the pressure of the reaction zones are in the range of about 1 to 30 atmospheres absolute.

6. The process according to claim 1, wherein the hydrogenation catalyst in step (a) is 5 weight percent copper on iron oxide.

7. The process according to claim 1, wherein the hydrogenation catalyst in step (a) is 5 weight percent cobalt on H-ZSM-5.

8. The process according to claim 1, wherein the catalyst in step (c) comprises palladium.

9. The process according to claim 8, wherein the catalyst in step (c) further comprises gold and potassium acetate.

10. The process according to claim 8, wherein the palladium is supported on a catalyst support selected from the group consisting of silica, alumina, silica-alumina, titania and zirconia.

11. The process according to claim 1, wherein the mole ratio of ethylene to molecular oxygen is about 4:1 or less.

12. The process according to claim 1, wherein in step (c) molecular oxygen is added in the form of air.

* * * * *